United States Patent [19]

Bach et al.

[11] Patent Number: 5,759,541
[45] Date of Patent: Jun. 2, 1998

[54] RECOMBINANT FIBRINOGENASES, THE PREPARATION AND USE THEREOF

[75] Inventors: Alfred Bach, Ladenburg; Heinz Hillen, Hassloch; Siegfried Bialojan, Oftersheim, all of Germany

[73] Assignee: BASF Aktiengesellschaft, Ludwigshafen, Germany

[21] Appl. No.: 684,862

[22] Filed: Jul. 25, 1996

Related U.S. Application Data

[63] Continuation of Ser. No. 361,705, Dec. 22, 1994, abandoned, which is a continuation of Ser. No. 966,040, filed as PCT/EP91/01361, Jul. 19, 1991 published as WO92/01794, Feb. 6, 1992, abandoned.

[30] Foreign Application Priority Data

Jul. 26, 1990 [DE] Germany ............ 40 23 699.4

[51] Int. Cl.$^6$ ............ A61K 38/48; A61K 35/14; C12P 21/06; C12N 9/50; C12N 9/64; C12N 1/20; C12N 15/00; C07H 21/04
[52] U.S. Cl. ............ 424/94.63; 424/94.6; 424/94.64; 435/69.1; 435/219; 435/226; 435/252.3; 435/320.1; 435/530; 435/381; 435/856; 536/23.2; 536/23.5

[58] Field of Search ............ 424/94.6, 94.64; 435/69.1, 219, 226, 252.3, 320.1; 530/381, 856; 536/23.2, 23.5

[56] References Cited

U.S. PATENT DOCUMENTS

| | | | |
|---|---|---|---|
| 4,027,012 | 5/1977 | Antonini | 424/542 |
| 4,585,653 | 4/1986 | Williams | 424/98 |
| 4,610,879 | 9/1986 | Markland, Jr. et al. | 424/94 |

FOREIGN PATENT DOCUMENTS

| | | |
|---|---|---|
| 0 395 375 | 10/1990 | European Pat. Off. . |
| WO90/06362 | 6/1990 | WIPO . |

OTHER PUBLICATIONS

Biochem. J. (1973) 131, pp. 799–807, Hatton, "Studies on the Coagulant Enzyme from Agkistrodon rhodostoma Venom".

Primary Examiner—Robert A. Wax
Assistant Examiner—Elizabeth Slobodyansky
Attorney, Agent, or Firm—Keil & Weinkauf

[57] ABSTRACT

Novel polypeptides having fibrinogenolytic properties and having amino acid sequences as SEQ ID NO: 3, SEQ ID NO: 4, SEQ ID NO: 5 and SEQ ID NO: 6 indicated in the Sequence Listing, the preparation and use thereof for controlling diseases.

28 Claims, 6 Drawing Sheets

Fig. 2
cDNA coding for ancord (sic)

```
CCATGGATGC ATGCGGCAAA GAGCTTCTGC GCAGAGTTGA AGCTATGATG CTGATCAGAG      60
TGCTAGCAAA CCTTCTGATA CTACAGCTTT CTTATGCACA AAAGTCTTCT GAACTGGTCA     120
TTGGAGGTGA TGAATGTAAC ATAAATGAAC ATCGTTTCCT TGTAGCCGTG TATGAAGGTA     180
CAAATTGGAC TTTTATCTGC GGTGGGGTTT TGATCCACCC GGAATGGGTG ATCACCGCTG     240
AACACTGTGC CAGGAGACGT ATGAACCTAG TCTTTGGTAT GCATAGAAAA AGTGAAAAAT     300
TTGACGATGA GCAGGAAAGA TACCCAAAGA AAAGGTACTT TATTCGCTGC AACAAAACCC     360
GTACCAGTTG GGACGAGGAC ATCATGTTGA TCAGGCTGAA CAAACCTGTT AACAACAGTG     420
AACACATCGC TCCTCTCAGC TTGCCTTCCA ACCCTCCCAT TGTGGGCTCA GATTGCCGTG     480
TTATGGGATG GGGCTCAATC AATCGACGTA TACACGTTTT GTCCGATGAA CCTCGTTGTG     540
CTAACATTAA CCTGCACAAT TTCACGATGT GTCATGGGCT TTTTCGAAAG ATGCCGAAGA     600
AAGGCAGAGT ATTGTGTGCA GGTGACCTGC GAGGACGCAG AGATTCATGT AATAGTGACT     660
CTGGGGACC TCTCATTTGT AATGAAGAAC TCCATGGCAT TGTAGCTAGG GGACCCAATC     720
CTTGTGCCCA GCCGAATAAG CCTGCCCTCT ACACCAGCGT CTACGATTAT CGTGACTGGG     780
TCAATAATGT TATTGCAGGA AATGCAACTT GCTCTCCATA AAAATAGTTA AGAGGAGAAA     840
```

Fig. 5
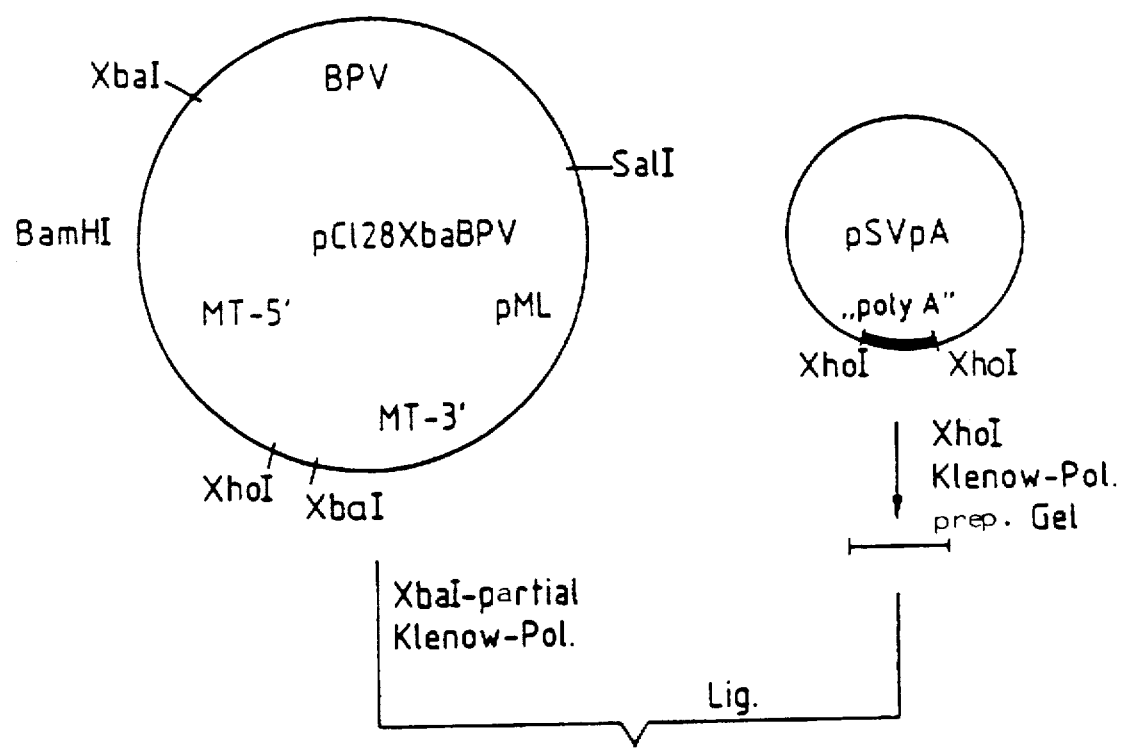
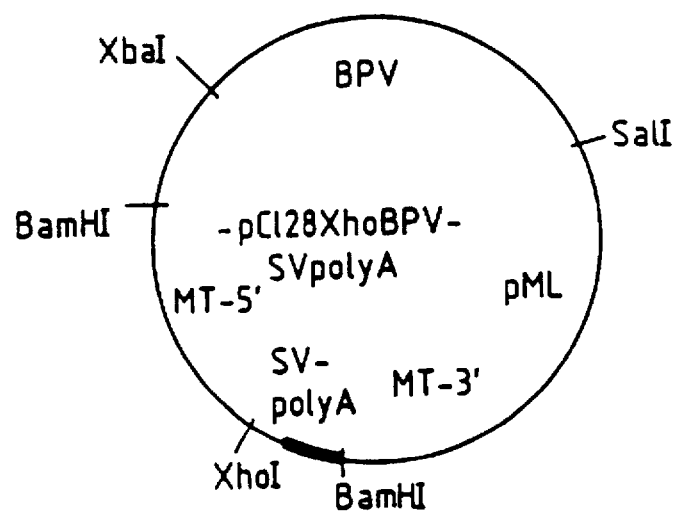

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
AATTCCATGG ATGCATGC                                              18
```

( 2 ) INFORMATION FOR SEQ ID NO: 2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

```
GTCTACGATT ATCGTGACTG GGTCAA                                     26
```

( 2 ) INFORMATION FOR SEQ ID NO: 3:

( i ) SEQUENCE CHARACTERISTICS:
        ( A ) LENGTH: 234 amino acids
        ( B ) TYPE: amino acid
        ( D ) TOPOLOGY: linear ( x i ) SEQUENCE DESCRIPTION: SEQ ID NO: 3:

```
Val  Ile  Gly  Gly  Asp  Glu  Cys  Asn  Ile  Asn  Glu  His  Arg  Phe  Leu  Val
  1              5                        10                       15
Ala  Leu  Tyr  Asp  Ser  Thr  Thr  Arg  Asn  Phe  Leu  Cys  Gly  Gly  Val  Leu
                20                       25                       30
```

| Ile | His | Pro | Glu | Trp | Val | Ile | Thr | Ala | Lys | His | Cys | Asn | Lys | Lys | Ser |
|---|---|---|---|---|---|---|---|---|---|---|---|---|---|---|---|
| | | 35 | | | | 40 | | | | | | 45 | | | |

| Met | Val | Leu | Tyr | Leu | Gly | Lys | His | Lys | Gln | Ser | Val | Lys | Phe | Asp | Asp |
|---|---|---|---|---|---|---|---|---|---|---|---|---|---|---|---|
| | 50 | | | | | 55 | | | | | 60 | | | | |

| Glu | Gln | Glu | Arg | Phe | Pro | Lys | Glu | Lys | His | Phe | Ile | Arg | Cys | Asn | Lys |
|---|---|---|---|---|---|---|---|---|---|---|---|---|---|---|---|
| 65 | | | | | 70 | | | | | 75 | | | | | 80 |

| Pro | Arg | Thr | Arg | Trp | Gly | Glu | Asp | Ile | Met | Leu | Ile | Arg | Leu | Asn | Lys |
|---|---|---|---|---|---|---|---|---|---|---|---|---|---|---|---|
| | | | | 85 | | | | | 90 | | | | | 95 | |

| Pro | Val | Xaa | Asn | Ser | Glu | His | Ile | Ala | Pro | Leu | Ser | Leu | Pro | Ser | Gly |
|---|---|---|---|---|---|---|---|---|---|---|---|---|---|---|---|
| | | | 100 | | | | | 105 | | | | | 110 | | |

| Pro | Pro | Ile | Val | Gly | Ser | Val | Cys | Arg | Val | Met | Gly | Trp | Gly | Ser | Ile |
|---|---|---|---|---|---|---|---|---|---|---|---|---|---|---|---|
| | | 115 | | | | | 120 | | | | | 125 | | | |

| Asn | Lys | Tyr | Ile | Asp | Val | Leu | Pro | Asp | Glu | Pro | Arg | Cys | Ala | Asn | Ile |
|---|---|---|---|---|---|---|---|---|---|---|---|---|---|---|---|
| 130 | | | | | 135 | | | | | 140 | | | | | |

| Asn | Leu | Tyr | Xaa | Tyr | Thr | Val | Cys | Arg | Gly | Val | Phe | Pro | Arg | Ile | Gly |
|---|---|---|---|---|---|---|---|---|---|---|---|---|---|---|---|
| 145 | | | | | 150 | | | | | 155 | | | | | 160 |

| Lys | Lys | Ser | Lys | Ile | Leu | Cys | Ala | Gly | Asp | Leu | Gln | Gly | Arg | Leu | Asp |
|---|---|---|---|---|---|---|---|---|---|---|---|---|---|---|---|
| | | | | 165 | | | | | 170 | | | | | 175 | |

| Ser | Cys | His | Cys | Asp | Ser | Gly | Gly | Pro | Leu | Ile | Cys | Ser | Glu | Glu | Phe |
|---|---|---|---|---|---|---|---|---|---|---|---|---|---|---|---|
| | | | 180 | | | | | 185 | | | | | 190 | | |

| His | Gly | Ile | Val | Tyr | Arg | Gly | Pro | Asn | Pro | Cys | Ala | Gln | Pro | Asp | Lys |
|---|---|---|---|---|---|---|---|---|---|---|---|---|---|---|---|
| | | 195 | | | | | 200 | | | | | 205 | | | |

| Pro | Ala | Leu | Tyr | Thr | Asn | Ile | Phe | Asp | His | Leu | His | Trp | Ile | Leu | Ser |
|---|---|---|---|---|---|---|---|---|---|---|---|---|---|---|---|
| 210 | | | | | 215 | | | | | 220 | | | | | |

| Ile | Val | Ala | Gly | Xaa | Ala | Thr | Cys | Tyr | Pro | | | | | | |
|---|---|---|---|---|---|---|---|---|---|---|---|---|---|---|---|
| 225 | | | | 230 | | | | | | | | | | | |

( 2 ) INFORMATION FOR SEQ ID NO: 4:

( i ) SEQUENCE CHARACTERISTICS:
( A ) LENGTH: 236 amino acids
( B ) TYPE: amino acid
( D ) TOPOLOGY: linear ( x i ) SEQUENCE DESCRIPTION: SEQ ID NO: 4:

| Val | Val | Gly | Gly | Asp | Glu | Cys | Asn | Ile | Asn | Glu | His | Arg | Phe | Leu | Ala |
|---|---|---|---|---|---|---|---|---|---|---|---|---|---|---|---|
| 1 | | | | 5 | | | | | 10 | | | | | 15 | |

| Leu | Val | Tyr | Ile | Thr | Ser | Gly | Phe | Leu | Cys | Gly | Gly | Thr | Leu | Xaa | His |
|---|---|---|---|---|---|---|---|---|---|---|---|---|---|---|---|
| | | | 20 | | | | | 25 | | | | | 30 | | |

| Pro | Glu | Trp | Val | Val | Ser | Ala | Ala | His | Cys | Ala | Arg | Gly | Glu | Ile | Glu |
|---|---|---|---|---|---|---|---|---|---|---|---|---|---|---|---|
| | | | 35 | | | | | 40 | | | | | 45 | | |

| Val | Phe | Phe | Gly | Val | His | Ser | Leu | Lys | Asp | Ile | Arg | Thr | Asn | Lys | Asp |
|---|---|---|---|---|---|---|---|---|---|---|---|---|---|---|---|
| | 50 | | | | | 55 | | | | | 60 | | | | |

| Val | Gln | Lys | Arg | Val | Ala | Lys | Glu | Met | Phe | Phe | Cys | Leu | Ser | Ser | Lys |
|---|---|---|---|---|---|---|---|---|---|---|---|---|---|---|---|
| 65 | | | | | 70 | | | | | 75 | | | | | 80 |

| Xaa | Tyr | Thr | Lys | Trp | Asp | Lys | Asp | Ile | Met | Leu | Ile | Lys | Leu | Asp | Ser |
|---|---|---|---|---|---|---|---|---|---|---|---|---|---|---|---|
| | | | | 85 | | | | | 90 | | | | | 95 | |

| Pro | Val | Xaa | Asn | Ser | Thr | His | Ile | Ala | Pro | Ile | Ser | Leu | Pro | Ser | Ser |
|---|---|---|---|---|---|---|---|---|---|---|---|---|---|---|---|
| | | | 100 | | | | | 105 | | | | | 110 | | |

| Pro | Pro | Ser | Val | Gly | Ser | Val | Cys | Arg | Val | Met | Gly | Trp | Gly | Val | Thr |
|---|---|---|---|---|---|---|---|---|---|---|---|---|---|---|---|
| | | 115 | | | | | 120 | | | | | 125 | | | |

| Thr | Ser | Pro | Xaa | Gly | Thr | Xaa | Pro | Ser | Val | Pro | His | Cys | Ala | Asn | Ile |
|---|---|---|---|---|---|---|---|---|---|---|---|---|---|---|---|
| | 130 | | | | | 135 | | | | | 140 | | | | |

| Asn | Ile | Leu | Asp | Tyr | Xaa | Val | Cys | Arg | Ala | Ala | Arg | Pro | Lys | Leu | Pro |
|---|---|---|---|---|---|---|---|---|---|---|---|---|---|---|---|
| 145 | | | | | 150 | | | | | 155 | | | | | 160 |

| Ala | Lys | Ser | Arg | Thr | Leu | Cys | Ala | Gly | Ile | Leu | Glu | Gly | Gly | Lys | Ser |

```
                              165                         170                           175
Ala Cys Asp Gly Asp Ser Gly Gly Pro Leu Asn Cys Asn Gly Glu Ile
            180                         185                     190

Gln Gly Ile Val Ser Trp Gly Gly Asn Ile Cys Ala Gln Pro Arg Lys
            195                         200                     205

Pro Ala His Tyr Xaa Lys Val Ala Asp Tyr Thr Asp Trp Ile Lys Ser
            210                     215                 220

Ile Ile Ala Gly Xaa Thr Thr Ala Thr Cys Pro Pro
225                     230                 235
```

(2) INFORMATION FOR SEQ ID NO: 5:

(i) SEQUENCE CHARACTERISTICS:
      (A) LENGTH: 236 amino acids
      (B) TYPE: amino acid
      (D) TOPOLOGY: linear (xi) SEQUENCE DESCRIPTION: SEQ ID NO: 5:

```
Val Ile Gly Gly Ala Glu Cys Asn Val Asn Glu His Arg Phe Leu Val
1               5                   10                  15

Ala Leu Tyr Asp Xaa Leu Thr Gly Thr Leu Gln Cys Gly Gly Thr Leu
            20                  25                  30

Ile His Pro Glu Trp Val Leu Thr Ala Ala His Cys Asp Arg Lys Ser
        35                  40                  45

Met Val Ile Tyr Leu Gly Met His Xaa Lys Ser Val Asn Asn Asp Asp
        50                  55                  60

Gln Gln Arg Arg Ser Ala Lys Glu Lys Tyr Phe Phe Ser Cys Ser Lys
65                  70                  75                  80

Ser Ile Ala Ala Trp Glu Lys Asp Ile Met Leu Ile Arg Leu Asp Ser
            85                  90                  95

Pro Val Xaa Asn Ser Thr His Ile Ala Pro Leu Ser Leu Pro Ser Arg
            100                     105                 110

Pro Pro Thr Val Gly Ser Val Cys Arg Val Met Gly Trp Gly Ala Ile
        115                     120                 125

Thr Ser Pro Lys Glu Thr Tyr Pro Glu Val Pro His Cys Thr Asp Ile
    130                     135                 140

Asn Leu Leu Xaa Tyr Ser Glu Cys His Gly Asp Phe Pro Arg Leu Arg
145                 150                     155                 160

Ala Thr Ser Arg Ile Leu Cys Ala Gly Val Leu Gln Gly Gly Ile Asp
            165                     170                     175

Thr Cys Asn His Asp Ser Gly Gly Pro Leu Ile Cys Asp Glu Gln Phe
            180                     185                     190

Gln Gly Ile Val Ser Trp Gly Pro Tyr Pro Cys Ala Gln Pro Arg Asn
            195                     200                 205

Ala Ala Ile Tyr Thr Lys Val Phe Asn Tyr Leu Val Trp Val Trp Ser
            210                     215                 220

Thr Ile Ala Gly Xaa Thr Thr Val Thr Cys Pro Pro
225                     230                 235
```

(2) INFORMATION FOR SEQ ID NO: 6:

(i) SEQUENCE CHARACTERISTICS:
      (A) LENGTH: 234 amino acids
      (B) TYPE: amino acid
      (D) TOPOLOGY: linear (xi) SEQUENCE DESCRIPTION: SEQ ID NO: 6:

```
Val Val Gly Gly Asn Glu Cys Asn Ile Asn Glu His Arg Phe Leu Val
```

|     |     |     |     |     |     |     |     |     |     |     |     |     |     |     |
| --- | --- | --- | --- | --- | --- | --- | --- | --- | --- | --- | --- | --- | --- | --- |
| 1   |     |     |     | 5   |     |     |     |     | 10  |     |     |     |     | 15  |
| Ala | Ile | Phe | Xaa<br>20 | Ser | Thr | Gly | Phe | Val<br>25 | Cys | Ala | Gly | Thr | Leu<br>30 | Ile | His |
| Pro | Glu | Trp<br>35 | Val | Val | Thr | Ala | Ala<br>40 | His | Cys | Glu | Ser | Thr<br>45 | Asp | Leu | Lys |
| Met | Lys<br>50 | Phe | Gly | Met | His | Ser<br>55 | Lys | Lys | Val | Gln | Asn<br>60 | Glu | Asp | Glu | Gln |
| Thr<br>65 | Arg | Asn | Ala | Lys | Glu<br>70 | Lys | Phe | Ile | Cys | Pro<br>75 | Asn | Lys | Lys | Asn | Asp<br>80 |
| Glu | Val | Leu | Asp | Lys<br>85 | Asp | Ile | Met | Leu | Ile<br>90 | Lys | Leu | Asn | His | Pro<br>95 | Val |
| Ser | Asn | Ser | Glu<br>100 | His | Ile | Ala | Pro | Leu<br>105 | Ser | Leu | Pro | Ser | Ser<br>110 | Pro | Pro |
| Ser | Val | Gly<br>115 | Ser | Phe | Cys | His | Ile<br>120 | Met | Gly | Trp | Gly | Ser<br>125 | Ile | Thr | Pro |
| Val | Lys<br>130 | Val | Thr | Phe | Pro | Asp<br>135 | Val | Pro | His | Cys | Ala<br>140 | Asn | Ile | Asn | Leu |
| Leu<br>145 | Glu | Glu | Ala | Glu | Cys<br>150 | His | Ala | Gly | Tyr | Pro<br>155 | Glu | Val | Leu | Ala | Glu<br>160 |
| Tyr | Arg | Thr | Leu | Cys<br>165 | Ala | Gly | Ile | Val | Gln<br>170 | Gly | Gly | Lys | Asp | Thr<br>175 | Cys |
| Met | Tyr | Asp | Ser<br>180 | Gly | Gly | Pro | Leu | Ile<br>185 | Cys | Asn | Glu | Gln | Val<br>190 | Gln | Gly |
| Ile | Val | Ser | Tyr<br>195 | Gly | Ala | His | Pro | Cys<br>200 | Gly | Gln | Pro | Leu | Lys<br>205 | Pro | Gly |
| Ile | Tyr | Thr<br>210 | Arg | Leu | His | Asp | Tyr<br>215 | Asn | Asp | Trp | Ile | Asn<br>220 | Ser | Ile | Met |
| Ala | Gly<br>225 | Asn | Thr | Ala | Val<br>230 | Thr | Cys | Pro | Pro |     |     |     |     |     |     |

( 2 ) INFORMATION FOR SEQ ID NO: 7:

( i ) SEQUENCE CHARACTERISTICS:
        ( A ) LENGTH: 25 amino acids
        ( B ) TYPE: amino acid
        ( D ) TOPOLOGY: linear ( x i ) SEQUENCE DESCRIPTION: SEQ ID NO: 7:

|     |     |     |     |     |     |     |     |     |     |     |     |     |     |     |
| --- | --- | --- | --- | --- | --- | --- | --- | --- | --- | --- | --- | --- | --- | --- |
| Val<br>1 | Ile | Gly | Gly | Asp<br>5 | Glu | Cys | Asn | Ile | Asn<br>10 | Glu | His | Pro | Phe | Leu<br>15 | Val |
| Ala | Val | Tyr | Glu<br>20 | Glu | Thr | Ala | Gly | Ala<br>25 |     |     |     |     |     |     |     |

( 2 ) INFORMATION FOR SEQ ID NO: 8:

( i ) SEQUENCE CHARACTERISTICS:
        ( A ) LENGTH: 1096 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Agkistrodon rhodostoma ( i x ) FEATURE:
        ( B ) LOCATION: 144 to 841
        ( D ) OTHER INFORMATION: the coding region shown in (2)(ix)(B)
            codes for the protein of SEQ ID NO: 3

( x i ) SEQUENCE DESCRIPTION: SEQ ID NO: 8:

| | | | | | |
|---|---|---|---|---|---|
| GAATTCCATG | GATGCATGCG | TTTGGGACTG | GGATCTTACA | GGCAAAGAGC | TTTCTGTGCA | 60
| GAGTTGAAGC | TATGGTGCTG | ATCAGAGTGC | TAGCAAACCT | TGTGATACTA | CAGCTTTCTT | 120
| ACGCACAAAA | GTCTTCTGAA | CTGGTCATTG | GAGGTGATGA | ATGTAACATA | AATGAACATC | 180
| GTTTCCTTGT | AGCCTTGTAT | GACAGTACGA | CTCGGAATTT | TCTCTGTGGT | GGGGTTTTGA | 240
| TCCATCCGGA | ATGGGTGATC | ACTGCTAAAC | ACTGCAACAA | GAAAGTATG | GTCCTATACC | 300
| TTGGTAAGCA | TAAACAAAGT | GTAAATTTG | ACGATGAGCA | GGAAAGATTC | CCAAAGGAGA | 360
| AGCACTTTAT | TCGCTGTAAC | AAACCCCGTA | CCAGATGGGG | CGAGGACATC | ATGTTGATCA | 420
| GGCTGAACAA | ACCTGTTAAC | AACAGTGAAC | ACATCGCTCC | TCTCAGCTTG | CCTTCCGGCC | 480
| CTCCCATTGT | GGGCTCAGTT | TGCCGTGTTA | TGGGATGGGG | CTCAATCAAT | AAATATATAG | 540
| ACGTTTTGCC | CGATGAACCT | CGTTGTGCTA | ATATTAACCT | GTACAATTAC | ACGGTGTGTC | 600
| GTGGAGTTTT | TCCAAGGATA | GGAAAGAAAA | GCAAAATATT | GTGTGCAGGT | GACCTGCAAG | 660
| GACGCCTAGA | TTCATGTCAC | TGTGACTCTG | GGGACCTCT | CATTTGTAGT | GAAGAATTCC | 720
| ATGGCATTGT | ATATCGGGGA | CCCAATCCTT | GTGCCCAACC | AGATAAGCCT | GCCCTCTACA | 780
| CCAACATCTT | CGATCATCTT | CACTGGATCC | TTAGCATTGT | GGCAGGAAAT | GCAACTTGCT | 840
| ATCCATAAAA | CCTTTTGAAA | TAGTTAAGTG | GAGAAAATGT | AACATATTAG | TAAATCTCTT | 900
| CTATATCCTT | GCATTGGAAC | ATATTCCCAG | GCTGTAAGCT | TTTAGACTC | AAATAGGACT | 960
| ACCTTGGAG | TAAGAAGTGC | TCAAAATAGT | GCTGCAGGGA | TCATGTCCCA | TTTAATTTCA | 1020
| GTTAAAACA | GTCTCCATAG | ATTGGAGGCC | TGTTTAGGGT | TAGGTGCAAA | TTTCTGACTC | 1080
| TAAATGGACC | ATTCCC | | | | | 1096

( 2 ) INFORMATION FOR SEQ ID NO: 9:

( i ) SEQUENCE CHARACTERISTICS:
        ( A ) LENGTH: 1333 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Agkistrodon rhodostoma ( i x ) FEATURE:
        ( B ) LOCATION: 231 to 935
        ( D ) OTHER INFORMATION: the coding region shown in (2)(ix)(B)
        codes for the protein of SEQ ID NO: 4

( x i ) SEQUENCE DESCRIPTION: SEQ ID NO: 9:

| | | | | | |
|---|---|---|---|---|---|
| ANCCCCCTTT | NNNGGNGGGG | GGGGNCCAGA | AGTTNCCCAG | ATTNCTTGGC | CACCCCGGTT | 60
| GCTTAATTTG | ATCAAATAAA | GTGCTGCTTG | ATCCAAGAAA | TTCTCCGCTT | GGGTTATCTG | 120
| ATTAGGCAAA | CAGCTTGCCA | CGCAGAGTTG | AAGCTATGGT | GCTGATCAGA | GTGCTAGCAA | 180
| ACCTTCTGAT | ACTACAACTT | TCTNACGCAC | AAAAGTCATC | TGAACNGGNC | GTTGGAGGTG | 240
| ATGAATGTAA | CATAAATGAA | CATCGTTTCC | TTGCACTCGT | GTATATCACT | AGTGGTTTTC | 300
| TCTGCGGTGG | GACTTTGANC | CACCCGGAAT | GGGTGGTCAG | TGCTGCACAT | TGCGCTAGGG | 360
| GAGAAATAGA | GGTATTCTTT | GGTGTGCATA | GCCTAAGGA | TATACGGACA | AATAAGGATG | 420
| TGCAGAAAAG | AGTCGCAAAG | GAGATGTTCT | TTTGCCTCAG | TAGCAAAAAC | TATACCAAAT | 480
| GGGACAAGGA | CATCATGTTA | ATCAAGCTGG | ACAGTCCTGT | TAACAACAGT | ACTCACATCG | 540
| CGCCTATCAG | CTTGCCTTCC | AGCCCTCCCA | GTGTGGGCTC | AGTTTGCCGT | GTTATGGGAT | 600

-continued

| | | | | | | |
|---|---|---|---|---|---|---|
| GGGGCGTAAC | CACATCTCCT | AATGGGACTA | TNCCCAGTGT | NCCTCACTGT | GCTAACATTA | 660 |
| ACATACTCGA | TTATNCGGTG | TGTCGAGCAG | CTAGGCCAAA | GTTGCCGGCG | AAAAGCAGAA | 720 |
| CATTATGTGC | TGGTATCCTG | GAAGGAGGCA | AAAGTGCATG | TGACGGTGAC | TCTGGGGGAC | 780 |
| CCCTCAACTG | TAATGGAGAA | ATCCAGGGCA | TTGTATCTTG | GGGGGGTAAT | ATTTGTGCTC | 840 |
| AACCGCGTAA | GCCTGCCCAC | TACNCCAAGG | TCGCCGATTA | TACTGATTGG | ATTAAGAGCA | 900 |
| TTATTGCAGG | AAATACAACT | GCAACTTGCC | CCCCGTGAAA | ATTTTTGAAA | AACTTAAGAG | 960 |
| GAGAAAATAC | ATCTCTTCTA | TATCCCTAGC | CATATTCAAT | TACATTGGAA | TATATTCCCA | 1020 |
| AGTTAACTCT | ACATCAACAA | AAAATCCTAC | NAAACAACAA | CAGAGAAGGA | GCAGATAAAA | 1080 |
| GAGATAAATG | GTACAAAATT | GAGAATCAAG | ACTTAAAGAT | GGAACTTAAG | AAAACAAGGA | 1140 |
| ACCATGATTT | AATCCTTGTG | GGGGGGGAAA | TCACAAGAAT | TGGAAAAAAA | CAACTTATCC | 1200 |
| CTTAGACAGC | AAACTAAATC | TGAGGACAAG | AAAACAGATT | GGATAAAATG | GACTGTAGAA | 1260 |
| ATGTCAGGAA | CATCGGAGAG | AAAGGAAATA | ATAAGAGAAG | CAAAAAAAAA | AAAAGCATGC | 1320 |
| ATCCATGGAA | TTC | | | | | 1333 |

( 2 ) INFORMATION FOR SEQ ID NO: 10:

( i ) SEQUENCE CHARACTERISTICS:
        ( A ) LENGTH: 988 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Agkistrodon rhodostoma ( i x ) FEATURE:
        ( B ) LOCATION: 197 to 904
        ( D ) OTHER INFORMATION: the coding region shown in (2)(ix)(B)
        codes for the protein of SEQ ID NO: 5

( x i ) SEQUENCE DESCRIPTION: SEQ ID NO: 10:

| | | | | | | |
|---|---|---|---|---|---|---|
| AACAATAAAG | NCTGCNTGAN | CAAGAAGCNN | CTGCTTAGCT | TATCTGATAA | GATTGACATG | 60 |
| TATCTCAAGC | TTAAGTTGGG | ACTGGGATCT | TACAGCAAAG | AGCTTTCCAC | GCAGAGTTGA | 120 |
| AGCTATGGTG | CTGATCAGAG | TGCTAGCAAA | CCTTCTGATA | CTACAGCTTT | CTTACGCACA | 180 |
| AAAGTCTTCT | GAACTGGTCA | TTGGAGGTGC | TGAATGTAAC | GTAAATGAAC | ATCGTTTCCT | 240 |
| TGTAGCCTTG | TATGACAATT | TGACTGGGAC | TTTGCAGTGT | GGTGGGACTT | TGATCCACCC | 300 |
| GGAATGGGTG | CTCACTGCTG | CGCACTGCGA | CAGGAAAAGT | ATGGTCATAT | ACCTTGGTAT | 360 |
| GCATAACAAA | AGTGTAAACA | ATGACGATCA | GCAGAGAAGA | TCCGCAAAGG | AGAAGTACTT | 420 |
| TTTTAGCTGT | AGCAAAAGCA | TTGCCGCATG | GGAAAAGGAC | ATCATGTTGA | TCAGGCTGGA | 480 |
| CAGTCCTGTT | AACAACAGTA | CACACATCGC | CCCTCTCAGC | TTGCCTTCCA | GACCTCCCAC | 540 |
| TGTGGGCTCA | GTTGCCGTG | TTATGGGATG | GGGCGCAATC | ACATCTCCTA | AAGAGACTTA | 600 |
| TCCTGAGGTC | CCTCATTGTA | CTGACATTAA | CCTGTTAAAT | TATTCGGAGT | GTCATGGAGA | 660 |
| TTTCCCACGG | TTGCGGGCGA | CAAGCAGAAT | ATTGTGTGCA | GGTGTCCTGC | AAGGAGGCAT | 720 |
| AGATACATGT | AATCATGACT | CTGGGGGACC | TCTCATCTGT | GATGAACAAT | TCCAGGGCAT | 780 |
| TGTATCTTGG | GGACCCTATC | CTTGTGCCCA | ACCGCGTAAC | GCTGCCATCT | ACACCAAAGT | 840 |
| CTTCAATTAT | CTTGTCTGGG | TCTGGAGCAC | TATTGCAGGA | AATACAACTG | TGACTTGCCC | 900 |
| CCCATGAAAA | CATTTTTATT | TCCACAAAGG | AGTTCCAAAA | GGAATTAAAA | CTAAATAATG | 960 |
| TGGTAAAAAA | AAAAAAAAAA | AAAAAAA | | | | 988 |

( 2 ) INFORMATION FOR SEQ ID NO: 11:

( i ) SEQUENCE CHARACTERISTICS:
        ( A ) LENGTH: 957 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Agkistrodon rhodostoma ( i x ) FEATURE:
        ( B ) LOCATION: 210 to 911
        ( D ) OTHER INFORMATION: the coding region shown in (2)(ix)(B)
            codes for the protein of SEQ ID NO: 6

( x i ) SEQUENCE DESCRIPTION: SEQ ID NO: 11:

```
CTNAATTNNA CAAAAAAGT  GCTGCTTGGT CAAGAGGTNC TCCGCTTCGG TTATCTGATT    60
AGATTGATAC GTATCTCAAG TATAAGTTTG GGACTGGGAT CTTACAGGAA AACAGCTTTC   120
CGTGCAGAGT TGAAGTTATG GTACTGATCA GAGTGCTAGC AAACCTTCTG ATACTACAGC   180
TTTCTTACGC ACAAAAGTCA TCTGAACTGG TCGTTGGAGG TAATGAATGT AACATAAATG   240
AACATCGTTT CCTTGTAGCC ATCTTTAACT CTACTGGGTT TGTCTGCGCT GGGACTTTGA   300
TCCACCCAGA ATGGGTGGTC ACTGCTGCAC ACTGCGAGAG TACGGATCTC AAGATGAAGT   360
TTGGTATGCA TAGCAAAAAG GTACAAAATG AGGATGAGCA GACAAGAAAC GCAAAGGAAA   420
AGTTCATTTG TCCCAATAAG AAAAACGATG AAGTACTGGA CAAGGACATT ATGTTGATCA   480
AGCTGAACCA TCCTGTTAGC AATAGTGAAC ACATCGCGCC TCTCAGCTTG CCTTCCAGCC   540
CTCCCAGTGT GGGCTCATTT TGCCATATTA TGGGATGGGG CTCAATCACA CCTGTTAAAG   600
TGACTTTCCC CGATGTCCCT CATTGTGCTA ACATTAACCT ACTCGATGAT GCAGAGTGTC   660
ATGCAGGTTA CCCTGAGGTG CTGGCAGAAT ACAGAACATT GTGTGCAGGT ATCGTGCAAG   720
GAGGCAAAGA TACATGTATG TATGACTCTG GAGGACCTCT CATCTGTAAT GAACAAGTCC   780
AGGGCATTGT ATCTTATGGG GCGCATCCTT GTGGCCAACC TCTTAAGCCT GGTATCTACA   840
CCAGGCTCCA TGATTATAAT GACTGGATCA ACAGCATTAT GGCAGGAAAT ACAGCTGTGA   900
CTTGCCCCCC GTGAAAACTT TAGTATCAGA AGGTTTGCTG CATGCATCCA TGAATTC      957
```

( 2 ) INFORMATION FOR SEQ ID NO: 12:

( i ) SEQUENCE CHARACTERISTICS:
        ( A ) LENGTH: 840 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 12:

```
CCATGGATGC ATGCGGCAAA GAGCTTCTGC GCAGAGTTGA AGCTATGATG CTGATCAGAG    60
TGCTAGCAAA CCTTCTGATA CTACAGCTTT CTTATGCACA AAAGTCTTCT GAACTGGTCA   120
TTGGAGGTGA TGAATGTAAC ATAAATGAAC ATCGTTTCCT TGTAGCCGTG TATGAAGGTA   180
CAAATTGGAC TTTTATCTGC GGTGGGGTTT TGATCCACCC GGAATGGGTG ATCACCGCTG   240
AACACTGTCG CAGGAGACGT ATGAACCTAG TCTTTGGTAT GCATAGAAAA AGTGAAAAAT   300
TTGACGATGA GCAGGAAAGA TACCCAAAGA AAAGGTACTT TATTCGCTGC AACAAAACCC   360
GTACCAGTTG GGACGAGGAC ATCATGTTGA TCAGGCTGAA CAAACCTGTT AACAACAGTG   420
AACACATCGC TCCTCTCAGC TTGCCTTCCA ACCCTCCCAT TGTGGGCTCA GATTGCCGTG   480
```

```
TTATGGGATG GGGCTCAATC AATCGACGTA TACACGTTTT GTCCGATGAA CCTCGTTGTG    540

CTAACATTAA CCTGCACAAT TTCACGATGT GRCATGGGCT TTTTCGAAAG ATGCCGAAGA    600

AAGGCAGAGT ATTGTGTGCA GGTGACCTGC GAGGACGCAG AGATTCATGT AATAGTGACT    660

CTGGGGGACC TCTCATTTGT AATGAAGAAC TCCATGGCAT TGTAGCTAGG GGACCCAATC    720

CTTGTGCCCA GCCGAATAAG CCTGCCCTCT ACACCAGCGT CTACGATTAT CGTGACTGGG    780

TCAATAATGT TATTGCAGGA AATGCAACTT GCTCTCCATA AAAATAGTTA AGAGGAGAAA    840
```

( 2 ) INFORMATION FOR SEQ ID NO: 13:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 13:

```
ATGATTACGA ATTCGAGCTC GGTACCCGGG GATCCTCTAG AGTCGACCTG CAGGCATGCA    60

AGCTTGGCAC TGGCC                                                     75
```

( 2 ) INFORMATION FOR SEQ ID NO: 14:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 14:

```
ATGATTACGC CAAGCTTGCA TGCCTGCAGG CTGACTCTAG AGGATCCCCG GGTACCGAGC    60

TCGAATTCAC TGGCC                                                     75
```

RECOMBINANT FIBRINOGENASES, THE PREPARATION AND USE THEREOF

This application is a continuation of application Ser. No. 08/361,705, filed on Dec. 22, 1994 which is a continuation of application Ser. No. 07/966,040, filed as PCT/EP91/01361, Jul. 19, 1991, published as WO92/01794, Feb. 6, 1992, both now abandoned.

The present invention relates to novel proteins with fibrinogenolytic properties, called fibrinogenases, the preparation and use thereof for the prophylaxis and therapy of diseases.

To date it has been possible to isolate from the venom of the Malayan pit viper (*Agkistrodon rhodostoma*) only one fibrinogen-cleaving enzyme having anticoagulant properties (Biochem. J. 131 (1973) 799). This protein is called Arvin, Arwin or ancrod in the literature.

The possible uses of this protein are limited because signs of resistance may appear after 6 to 8 weeks and are presumably attributable to the production of ancrod-neutralizing antibodies. Hemorrhagic complications also occur in a few cases.

We have now found, and prepared pure, other proteins with fibrinogenolytic properties.

The present invention relates to glycosylated, partially glycosylated or non-glycosylated polypeptides with the amino-acid sequences 1, 2, 3, 4 and 5 given in the sequence listing, where Xaa and Xab are residues of natural α-amino acids, and to the allelic variants thereof which are identical in more than 95% of the amino-acid positions to the indicated sequences.

The residue Xaa is Asn, Gln, Ser, Thr, Gly, Asp, Glu, Lys, Arg or Pro, but preferably Asn, Gln, Ser and Thr and, in particular, Asn and Gln. Xab is preferably Phe, Tyr, Leu, Ile, Ala, Val, Thr or Ser.

The present invention also relates to DNA sequences which code for the abovementioned proteins, and to vectors which contain these DNA sequences. Preferred DNA sequences are depicted as sequences Nos. 6 to 9 in the sequence listing.

The proteins according to the invention can be prepared by known methods of genetic manipulation.

Thus, it is possible to isolate from the glandular tissue of a Malayan pit viper (*Agkistrodon rhodostoma*) mRNA and to convert it into double-stranded cDNA. A cDNA library is set up after insertion of this cDNA into a commercial cloning vector, eg. λ gt 10. The methods used for this can be found, for example, in Maniatis et al., Molecular Cloning, CSH Press (1982). The screening of such gene banks with radiolabeled oligonucleotide probes or radiolabeled DNA fragments is also now a widely used and described method. This method can be used to isolate and characterize a cDNA clone which has homology with the oligonucleotide probe or with radiolabeled DNA fragments, and is described in DNA cloning, Vol. I, IRL Press, 1985.

The cDNA which has been characterized in this way can easily be obtained using restriction enzymes. The fragments resulting from this can be used, where appropriate in combination with chemically synthesized oligonucleotides, adaptors or gene fragments, to clone the sequences coding for the protein. The gene fragments or synthetic DNA sequences are incorporated into cloning vectors, eg. the commercial plasmids M13mp or pkk-223-3, in a conventional manner. The genes or gene fragments can also be provided with suitable control regions which have been chemically synthesized or isolated from bacteria, phages, eukaryotic cells or viruses thereof and which make expression of the proteins possible.

The transformation or transfection of suitable host organisms with the hybrid plasmids obtained in this way is likewise known and described in detail (M. Wigler et al., Cell 16 (1979) 777–785; F. L. Graham and A. J. van der Eb, Virology 52 (1973) 456–467). The hybrid plasmids can also be provided with appropriate signal sequences to allow the polypeptides to be secreted into the medium.

Vectors which can be used for expression in mammalian cells are those which place the gene to be expressed, in this case the cDNA which codes for one of the fibrinogenases described in the sequence listing, under the control of the mouse metallothionein or viral SV40 promoter (J. Page Martin, Gene, 37 (1985) 139–144). The presence of the methionine start codon and of the leader/prosequence of the gene for the appropriate protein is necessary for expression. Clones which contain copies of these vectors as episomes or integrated in the genome are then isolated. Integration and expression of the foreign gene on the basis of the bovine papilloma virus are particularly advantageous. It is possible to construct shuttle vectors in conjunction with prokaryotic sequences which code for replication in bacterial cells and for antibiotic resistance. The plasmid is initially constructed and multiplied in bacterial cells and is then transferred into the eukaryotic cells, eg. into the mouse fibroblast cell line c127.

It is also possible to use other cell systems, eg. yeast and other fungi, insect cells and animal and human cells such as CHO, COS, L and 293 cells, in conjunction with suitable expression vectors for the expression of the cloned cDNA.

These eukaryotic expression systems have the advantage that they are able to secrete their products efficiently and usually in native form. They also have the ability to carry out post-translational modification on their products.

Thus, on expression in eukaryotic cells, the described fibrinogenases acquire glycoside side-chains. These side-chains are absent in the polypeptides produced in bacteria. The glycoside side-chains can also be removed completely or partially using appropriate glycosidases. Most eukaryotic proteins expressed in bacteria, result as denatured inclusion bodies in the cell and must be renatured by appropriate methods. In addition, bacteria are often incapable of eliminating the initiator amino acid methionine from the finished protein. These difficulties can be avoided by using secretion systems (Donald Oliver, Ann. Rev. Microbiol. 39, (1985) 615–48;

John Ghrayeb et al. The EMBO Journal 3 (1984) 2437–2442.

However, because of the degeneracy of the genetic code, it is also possible to use other DNA sequences, eg. chemically synthesized genes with different DNA sequences, for the expression of the described fibrinogenases. Application of established methods of mutagenesis to the cloned genes allows production of variants of these fibrinogenases with a similar action.

The resulting polypeptides are purified from the culture medium by chromatography, eg. affinity chromatography on arginine-Sepharose®, Matrex-RedA-Sepharose®, heparin-Sepharose® or ion exchange materials in a conventional manner (Lit.: Guide to Protein Purification, Murray P. Deutscher [ed], Academic Press 1990).

The purification of the fibrinogenases can likewise be purified [sic] directly from the venom of *A. rhodostoma* by a combination of suitable chromatographic methods, preferably using Matrex-redA-Sepharose®, heparin-Sepharose®, arginine-Sepharose®, conA-Sepharose®, Q-Sepharose®, S-Sepharose® and chromatofocussing as described in Example 5. Particularly suitable for the final purification are HPLC methods.

The present invention also relates to drugs which contain the proteins prepared according to the invention, where appropriate in a pharmaceutically tolerated carrier or excipient. The drugs can also contain combinations of the proteins prepared according to the invention with other pharmacologically active substances such as thrombolytics (tPA, streptokinase), hirudin or thromboxane receptor antagonists.

Further embodiments of the invention are described in detail in the Examples.

For methods of genetic manipulation, reference may be made to, for example, the handbook by Maniatis et al., Molecular Cloning, Cold Spring Harbor Laboratory, 1982 or DNA cloning Vol. I–III, IRI [sic] Press 1985–87, edited by D. M. Glover.

The polypeptides according to the invention are suitable for the treatment of glomerulonephritis, myocardial infarct, non-ischemic stroke, disturbances of peripheral arterial blood flow (especially atherosclerosis obliterans, thrombangitis obliterans, diabetic microangiopathy and Raynaud's disease), unstable angina pectoris, deep vein thrombosis and other thromboses, rethrombosis after thrombolysis or vascular surgery, such as angioplasty, and for preventing thromboses in extra-corporeal circulations.

BRIEF DESCRIPTION OF THE DRAWINGS

FIG. 2 cDNA coding for ancrod.

FIG. 5 Flow sheet of the method for the preparation of linearized CL28XhOBPV expression vector.

EXAMPLE 1
Isolation of a fibrinogenase cDNA clone from the Malayan pit viper (*Agkistrodon rhodostoma*)

1 g of venom gland tissue from a 5-year old snake of the genus [sic] *Agkistrodon rhodostoma* was disrupted in 6M guanidinium thiocyanate, 5 mM sodium citrate (pH 7.0), 0.1M 2-mercaptoethanol, 0.5% sarkosyl in an ULTRA-TURRAX®. Large cell detritus was removed by centrifugation at 3000 rpm. The RNA was removed by centrifugation through a 5.7M CsCl cushion at 45,000 rpm overnight. The polyA$^+$-containing RNA fraction was then isolated by affinity chromatography on oligo(dT)-cellulose.

Figure 1:
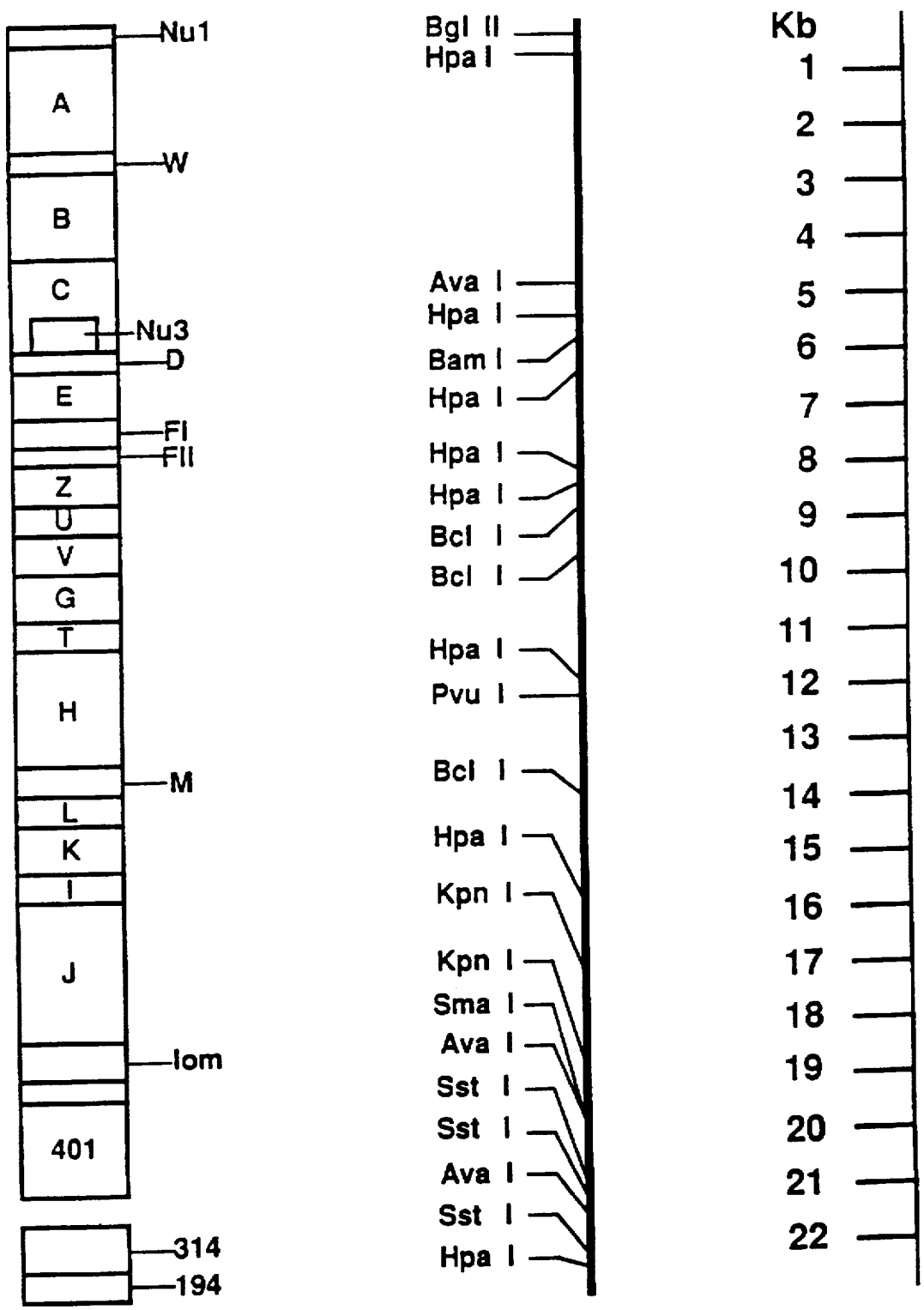
FIGS. 1a and 1b Commercial phage vector gammagt10.
Figure 1B:
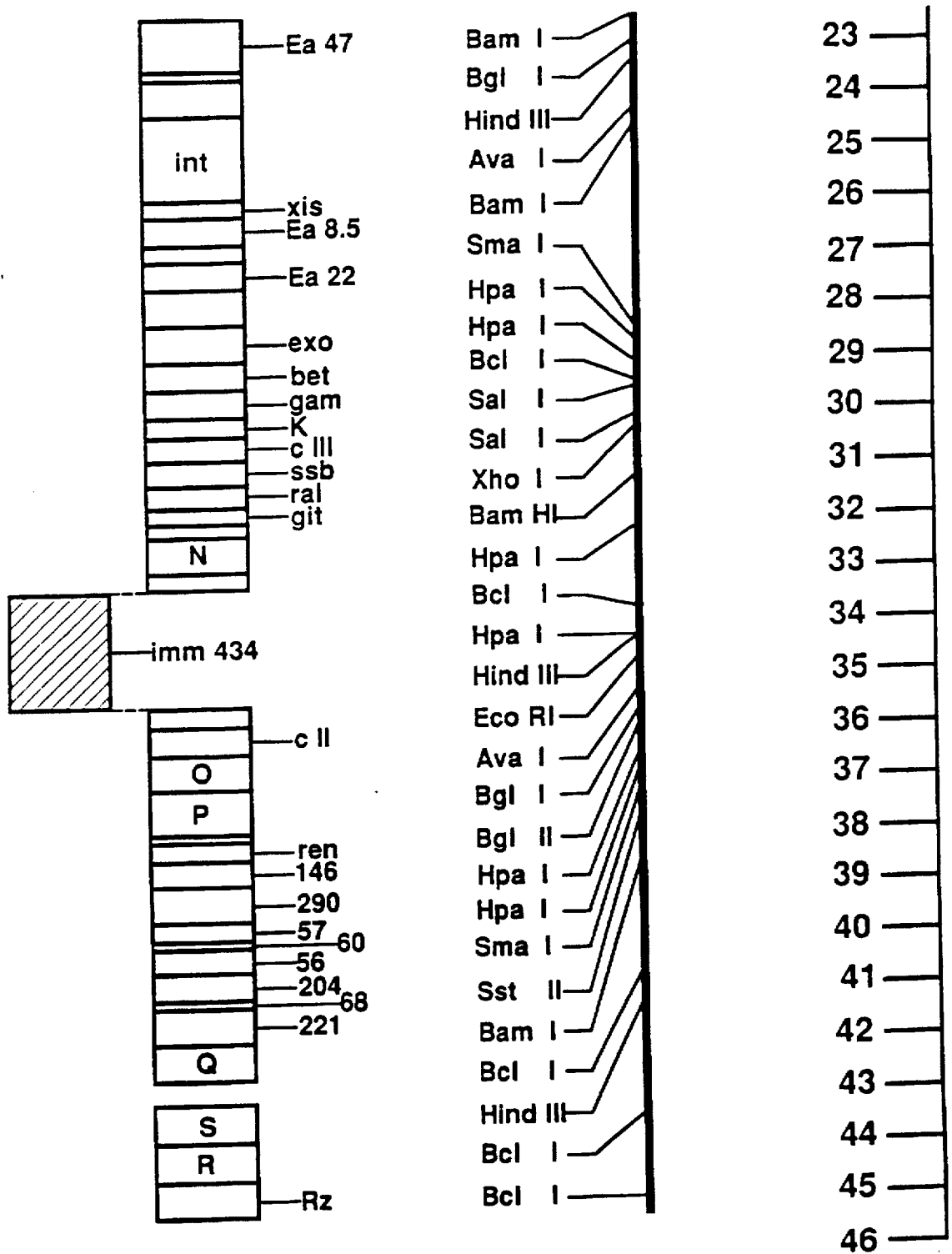

The polyA$^+$ RNA was converted into single-stranded cDNA using AMV reverse transcriptase and oligo(dT)12-18 as primer. The second strand was synthesized using *E.coli* DNA polymerase I. An EcoRI adaptor, of the sequence 5'AATT CCATGG ATG CATGC 3' SEQ ID NO: 1—was attached to the double-stranded cDNA using T4-DNA ligase. The commercial phage vector λ gt10 (FIGS. 1a, 1b) was linearized with the restriction enzyme EcoRI. The two DNAs were ligated together and packaged with the commercial packaging extract to give infectious phages. The recombinant phages were plated out with *E.coli* C 600 Hfl on NZYDT plates and incubated at 37° C. overnight. The resulting cDNA library contained 2×10$^6$ independent clones. Amplification of the cDNA library by conventional methods was followed by plating out of 500,000 phages with C 600 Hfl cells. The phages were transferred to nitrocellulose filters, lyzed with 0.5N NaOH/1.5M NaCl, and the denatured DNA was firmly bound to the filter by baking at 80° C. for 2 hours. The filters were prehybridized in 6×SET buffer (1×SET=0.15M NaCl, 15 mM tris/HCl, pH 7.4, 1 mM EDTA), 0.1% SDS and 5×Denhardt's solution (100× Denhardt=1 g of Ficoll, 1 g of polyvinylpyrrolidone, 1 g of BSA per 50 ml) at 68° C. for 4 h.

Hybridization was carried out with a nick-translated cDNA (FIG. 2) which codes for ancrod protein.

The filters were incubated in a solution which contained 2×SET, 0.1% SDS, 30% formamide, 5×Denhardt's and 10% dextran sulfate at 42° C. overnight while shaking gently. They were then washed several times with 2×SET/0.1% SDS at 42° C., dried and exposed to an X-ray film. Clones which gave a radioactive response in the screening were isolated and cultured further in order to obtain the corresponding phage DNA.

Phage DNA was prepared by incubating the purified phages with protenase [sic] K (ad 60 µg/ml) at 55° C. for 1 h and subsequent phenol/chloroform extraction. Addition of 3 volumes of ethanol (−20° C.) resulted in precipitation of the phage DNA, which was transferred with a sterile injection needle into 70% ethanol, washed and briefly sedimented. The pellet was briefly dried in air and then suspended in TE buffer.

The purified phage DNA was transferred to nitro-cellulose filters, renatured, reneutralized, baked and prehybridized as described above. Hybridization was then carried out under stringent conditions, using a radio-labeled oligonucleotide probe which was homologous to the ancrod-encoded [sic] cDNA: SEQ ID NO: 2

5' GTC TAC GAT TAT CGT GAC TGG GTC AA 3'

The filters were incubated in a solution which contained 2×SET, 0.1% SDS, 30% formamide, 5×Denhardt's and 10% dextran sulfate at 42° C. overnight while shaking gently. They were then washed several times in 2×SET/0.1% SDS at 60° C., dried and exposed to an X-ray film.

The DNA which did not hybridize under these conditions was subconed [sic] in the single-stranded phage MB for further analysis.

EXAMPLE 2
Preparation of single-stranded DNA which codes for ancrod

Figure 3:
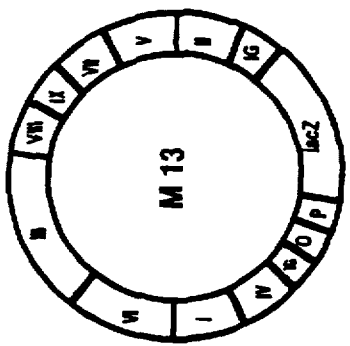
FIG. 3 M13mp18 and M13mp19 cloning vectors.

The starting point were [sic] the phage DNA which did not hybridize with the ancrod-specific oligonucleotide as described in Example 1. They were each separately cut preparatively with the restriction enzyme Eco RI. The Eco RI fragments which contained the cDNA inserts were eluted from the gel by electrophoresis. 30 ng of each of these fragments were ligated at 4° C. for 12 h with 100 ng of the commercial cloning vector M13mp18 or M13mp19 (FIG. 3) which had been cut with Eco RI. The volume of the ligation mixture was 10 µl. Ligation was stopped by heating at 80° C. for 5 min.

$\frac{1}{10}$ of the volume of each ligation mixture was employed to transform 100 µl of competent SR 101 cells. After the transformation was complete, 60 µl of 0.2M IPTG solution and 120 µl of XGal (20 mg/ml) were added to the transformation mixture. The resulting mixture was plated out in NZYDT top agar on NZYDT agar plates containing 200 µl of SR101 cells (OD$_{600}$=1). The NZYDT medium is commercially available (GIBCO-BRL). Clones which contained cDNA inserts were identifiable because the plaques were not stained blue. DNA sequence analysis (Sanger et al., Proc. Natl. Acad. Sci. USA 74, (1977) 5463–67) was used to elucidate the sequence of this cDNA insert (SEQ ID No. 8 to SEQ No. 11).

Figure 4:
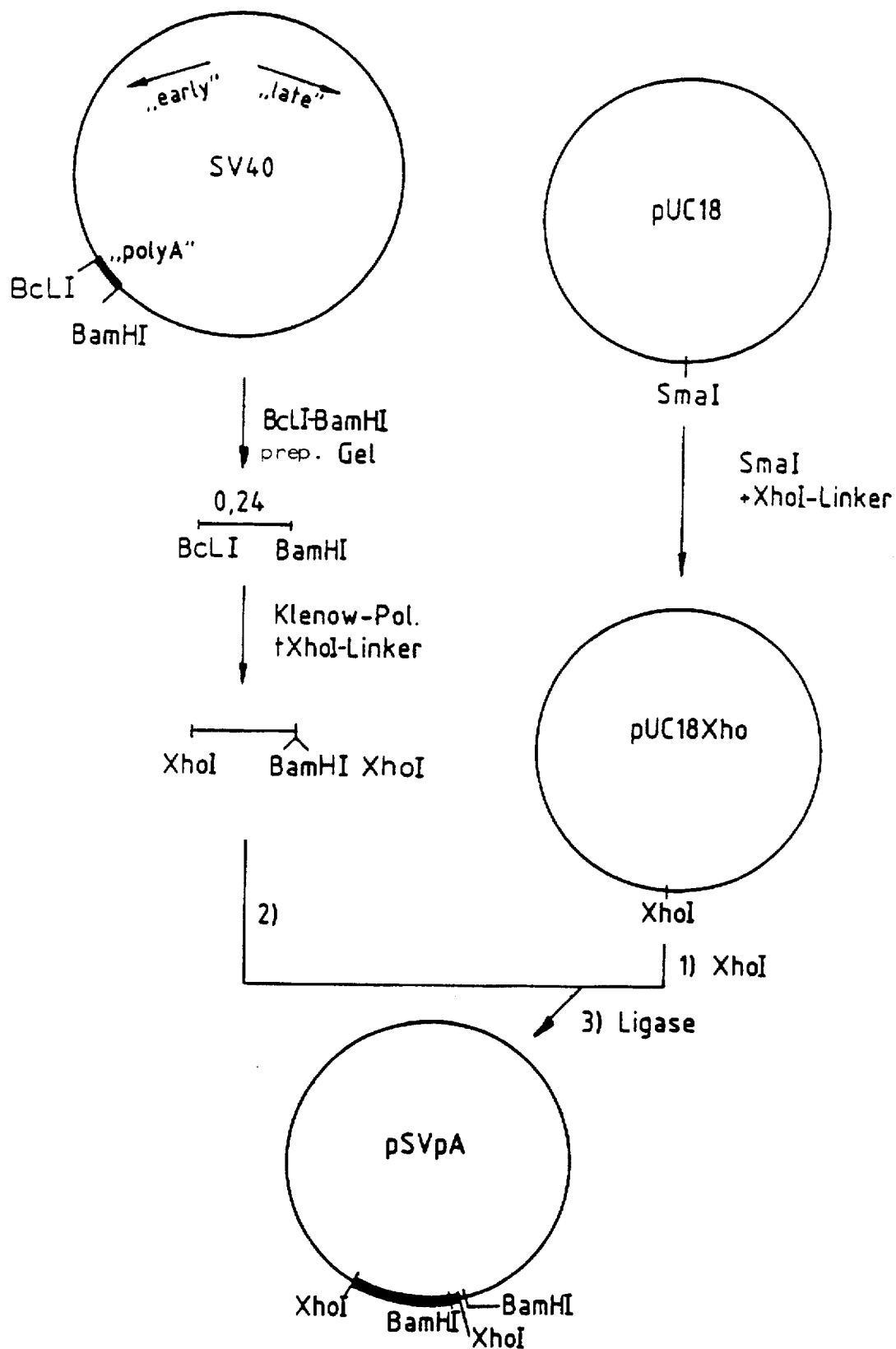
FIG. 4 Flow sheet of the method for the preparation of the 0.24 kb SV40 fragment.

EXAMPLE 3
Construction of vectors for the expression of ancrod in eukaryotic cells SV40 DNA was cut with the restriction enzymes BamHI and BclI, and the 0.24 kb fragment was prepared by gel electrophoresis (FIG. 4). The ends were filled in with the Klenow fragment in the presence of the four deoxynucleotide triphosphates dATP, dCTP, dGTP and dTTP. XhoI linkers were then ligated on.

In parallel the commercial vector pUC18 was linearized with SmaI. XhoI linkers were then likewise attached. The DNA of this vector (puCl8Xho) was linearized with XhoI, treated with alkaline phosphatase and ligated to the 0.24 kb XhoII [sic] SV40 fragment (see above). The result was pSVpA.

pSVpA DNA was cleaved preparatively with XhoI and incubated with Klenow polymerase in the presence of the four dNTPs as above. The 0.24 kb fragment was isolated from the gel.

At the same time, the eukaryotic expression vector CL28XhoBPV, produced by ligation of CL28x and pB2-2 (Reddy et al. DNA 6, (1987) 461–72) was partially cut with the restriction enzyme XbaI, ie. the incubation time was restricted so as to result in molecules cleaved at only one of the two XbaI recognition sequences, ie. linearized (FIG. 5). The mixture was then reacted with Klenow polymerase and dNTPs as described. The linear molecules were subsequently isolated by gel electrophoresis.

The linear pCL28XhoBPV fragments were then ligated with the pretreated 0.24 kb SV40 fragment. After transformation and screening of minilysates, a clone which carried the SV40 fragment in the former XbaI site located about 0.15 kB [sic] 3' of the XhoI site was isolated; this DNA (pCL28XhoBPV-SVpolyA) carried the SV40 transcription stop signals of the early genes.

Plasmid DNA from pCL28XhoBPV-SVpolyA was linearized with XhoI and treated with alkaline phosphatase. At the same time, the cDNA inserts which did not hybridize with the Ancrod-specific oligonucleotide as described in Example 2 were provided with Xho linkers using T4 ligase. The two fragments were connected together using T4 ligase. After transformation and analysis of minilysates, a clone which contained the cDNA inserts singly and in the correct orientation was isolated: pCL28BPV-fibrogenase [sic] I–IV.

EXAMPLE 4
Transfection and establishment of cell lines c127I cells (J. Virol. 26 (1978) 292; ATCC catalog of cell lines and hybridomas 5th edition, 1985, p.142) were transfected with BPV expression plasmids using the calcium phosphate coprecipitation method (Virology 52 (1973), 456, DNA cloning; Volume II, ed. D. M. Glover IRL Press, (1985) 143ff and 213).

DMEM (Dulbeccos's Modified Eagles Medium)+10% FCS (fetal calf serum) in 60 mm Petri dishes was inoculated with $5 \times 10^5$ C127I cells. The next day the medium was changed to MEM (Modified Eagles Medium) containing 25 nM Hepes+10% FCS. A Ca phosphate coprecipitate was formed with $10^{-5}$ g of CsCl-purified plasmid DNA and was cautiously placed on the C172I cells. The cells were incubated at 37° C., 7% $CO_2$ for 4 h. A subsequent glycerol shock treatment considerably increased the efficiency of transfection. For this, 4 h after addition of the precipitate the medium was aspirated off from the cells. The cells were incubated with 2 ml each [sic] of 15% glycerol/HBS (DNA cloning Vol. II, page 152) in a 60 mm Petri dish at room temperature for 3 min. The glycerol/HBS solution was aspirated off and the cell lawn was washed with 3 ml of DMEM+10% FCS. The cells were incubated with DMEM+10% FCS at 37° C., 7% $CO_2$. The DMEM+10% FCS was aspirated off and replaced by fresh three times a week. After 2–3 weeks, the transfected cells which contain the BPV genome were evident as collections of transformed cells, called foci.

After the foci had been subcloned, the medium supernatants from the individual subclones were tested for fibrinogen-cleaving activity by conventional methods.

For production, after the cell lines had reached confluence they were maintained in serum-free DMEM. The novel fibrinogenases can be purified by conventional methods from the serum-free cell culture supernatant obtained in this way and used for pharmacological and chemical analyses.

EXAMPLE 5
Isolation and purification of a fibrinogen-cleaving enzyme (Fibrinogenase V) from the venom of *Agkistrodon rhodostoma*

550 mg of crude venom (dry substance) from *Agkistrodon rhodostoma* were taken up in 20 ml of 20 mM $Na_2HPO_4$, 0.01% Tween® 80, 500 mM NaCl, pH 7.0 (=buffer A).

a) Chromatography on Matrex Red A-Sepharose®:

A chromatography column (diameter 2.5 cm, length 5.1 cm) was packed with 25 ml of Matrex red A-Sepharose® (from Amicon). The column was equilibrated with 100 ml of buffer A and then loaded with the dissolved crude venom. The column was washed with 45 ml of buffer A (flow rate 120 ml/h) and then eluted with 85 ml of buffer B, which was composed of 20 mM $Na_2HPO_4$, 2M NaCl, 0.01% Tween, pH 7.0. The UV-active fraction (280 nm) was collected.

The eluate was dialyzed twice against 2.5 l of 20 mM $Na_2HPO_4$, 0.01% Tween® 80, pH 7.0 (=buffer C) in a dialysis tube (Visking size 8.32/32) for 2 h each time. The conductivity of the dialyzed tubes [sic] was about 2.2 mS/cm (4° C.).

b) Chromatography on arginine-Sepharose®:

A chromatography column (diameter 2.5 cm, length 10 cm) was packed with arginine-Sepharose® (from Pharmacia) and equilibrated with 200 ml of buffer C.

The dialyzed eluate (vol. about 140 ml) from the Matrex red A-Sepharose® was loaded on the column with a flow rate of 120 ml/h.

The flow-through from the column (about 180 ml) was collected and processed further. Still bound to the column was, inter alia, ancrod which can be obtained by elution with arginine salts.

c) Chromatofocussing

A chromatography column (diameter 0.5 cm, length 5 cm) was packed with 1 ml of PBE® 94 gel material (from Pharmacia). The column was equilibrated with 5 column volumes of 20 mM tris/HCl, 0.01% Tween® 80, pH 8.0 (=buffer D).

The column was loaded with 20 ml of the flow-through from the arginine-Sepharose®.

The chromatography was carried out with a linear gradient from buffer D to 20 mM acetic acid/HCl, 0.01% Tween® 80, pH 2.0 (=buffer E) in 25 min with a flow rate of 1 ml/min. After this time, the column was eluted with buffer E for a further 13 min. The UV-active fraction (280 nm) eluted during this was collected. About 1 ml of a protein solution which contained, according to protein determination (method: Anal. Biochem. 153, 267–271), about 0.04 mg/ml was obtained.

d) Characterization of the purified fibrinogenase V d1) SDS gel electrophoresis

Comparing with standard proteins, the protein solution showed a main band (about 70 to 90%) at ~42,000 Dalton.

d2) N-terminal sequencing

The N-terminal sequence of the purified protein solution was determined (see sequence listing, SEQ ID NO: 7).

d3) Fibrinogenase assay

Fibrinogenase activities were determined by converting fibrinogen with the enzyme to be assayed into deAA fibrinogen.

This reaction was associated with an increase in turbidity which was followed by photometry (DD [sic] 340 nm).

The activity was quantified by calibration with an ancrod standard (Arwin®) of 3000 U/mg.

The fibrinogenase activity of the purified enzyme was about 500 U/mg.

Brief Description of SEQ ID NOS: 8–11

SEQ ID NO. 8: 1096 nucleotide sequence corresponding to amino-acid sequence No. 3
Strandedness: double-stranded
Topology: linear
Molecule Type: cDNA to mRNA
Original Source: *Agkistrodon rhodostoma*
The region coding for the protein of sequence No. 3 starts at base 144 and terminates at base 841.

SEQ ID NO. 9: 1333 nucleotide sequence corresponding to amino-acid sequence No. 4
Strandedness: double-stranded
Topology: linear
Molecule type: cDNA to mRNA
Original source: *Agkistrodon rhodostoma*
The region coding for the protein of sequence No. 4 starts at base 231 and terminates at base 935.

SEQ ID NO. 10: 988 nucleotide sequence corresponding to amino-acid sequence No. 5
Strandedness: double-stranded
Topology: linear
Molecule type: cDNA to mRNA
Original source: *Agkistrodon rhodostoma*
The region coding for the protein of sequence No. 5 starts at base 197 and terminates at base 904.

SEQ ID NO. 11: 957 nucleotide sequence corresponding to amino-acid sequence No. 6
Strandedness: double-stranded
Topology: linear
Molecule type: cDNA to mRNA
Original source: *Agkistrodon rhodostoma*
The region coding for the protein of sequence No. 6 starts at base 210 and terminates at base 911.

---

We claim:

1. An isolated and purified polypeptide from *Agkistrodon rhodostoma* having an amino acid sequence set forth in SEQ ID NO: 3, SEQ ID NO: 4, SEQ ID NO: 5 or SEQ ID NO: 6, in which Xaa in the amino acid sequences represents a residue of a natural α-amino acid.

2. An isolated and purified polypeptide obtained from the crude venom of *Agkistrodon rhodostoma* by chromatography on matrex red A-Sepharose® ion-exchange medium and arginine-Sepharose® ion-exchange medium and subsequent chromatofocusing with the gel material PBE® 94, which exhibits a main band with a molecular weight of about 42,000 dalton on SDS-PAGE, has a fibrinogenase activity of about 500 U/mg and has the N-terminal amino acid sequence shown in SEQ ID NO: 7.

3. An isolated and purified DNA sequence which codes for a polypeptide as defined in claim 1.

4. A recombinant DNA molecule comprising a DNA sequence as defined in claim 3 which is functionally connected to an expression control system which makes expression possible in suitable host systems.

5. A recombinant DNA molecule as defined in claim 4, wherein the expression control sequence is an *E.coli* promoter system, a promoter system of an *E.coli* bacteriophage, a yeast or fungus expression control sequence or another eukaryotic expression control sequence.

6. A host cell which contains at least one recombinant DNA molecule as defined in claim 5.

7. A host cell of claim 6, wherein said cell is a bacterial, yeast, fungal, animal or human cell.

8. A method for producing a polypeptide having an amino acid sequence set forth in SEQ ID NO: 3, SEQ ID NO: 4, SEQ ID NO: 5 or SEQ ID NO: 6 which comprises culturing a cell of claim 7 and recovering said polypeptide.

9. A method for preventing or treating thromboembolic diseases or glomerulonephritis, which comprises administering to a patient in need thereof a disease-preventing or disease-treating effective amount of the polypeptide of claim 1.

10. An isolated and purified DNA sequence which codes for a polypeptide as defined in claim 2.

11. A recombinant DNA molecule comprising a DNA sequence as defined in claim 10 which is functionally connected to an expression control system which makes expression possible in suitable host systems.

12. A recombinant DNA molecule as defined in claim 11 wherein the expression control sequence is an *E. coli* promoter system, a promoter system of an *E. coli* bacteriophage, a yeast or fungus expression control sequence or another eukaryotic expression control sequence.

13. A host cell which contains at least one recombinant DNA molecule as defined in claim 12.

14. A host cell of claim 13, wherein said cell is a bacterial, yeast, fungal, animal or human cell.

15. A method for preventing or treating thromboembolic diseases or glomerulonephritis, which comprises administering to a patient in need thereof a disease-preventing or disease-treating effective amount of the polypeptide of claim 2.

16. The polypeptide of claim 1 wherein Xaa is selected from the group consisting of Gln, Asn, Ser, Thr, Gly, Asp, Glu, Lys, Arg and Pro.

17. The polypeptide of claim 1 wherein Xaa in positions 31, 135, 150 and 213 of the amino acid sequence represented by SEQ ID NO: 4 is selected from the group consisting of Phe, Tyr, Leu, Ile, Ala, Thr and Ser.

18. The polypeptide of claim 1 wherein Xaa is Asn or Gln.

19. The polypeptide of claim 18 wherein Xaa is Asn.

20. The polypeptide having an amino acid sequence set forth in SEQ ID NO: 3, wherein Xaa is selected from the group consisting of Asn, Gln, Ser, Thr, Gly, Asp, Lys, Arg and Pro.

21. The polypeptide of claim 20 wherein Xaa is Asn or Gln.

22. The polypeptide of claim 21 wherein Xaa is Asn.

23. The polypeptide having an amino acid sequence set forth in SEQ ID NO: 6, wherein Xaa is selected from the group consisting of Asn, Gln, Gly, Asp, Lys, Arg and Pro.

24. The polypeptide of claim 23 wherein Xaa is Asn or Gln.

25. The polypeptide of claim 24 wherein Xaa is Asn.

26. The polypeptide of claim 1 wherein Xaa in position 20 of the amino acid sequence represented by SEQ ID NO: 6 is selected from the group consisting of Phe, Tyr, Leu, Ile, Ala, Thr and Ser.

27. An isolated and purified deoxyribonucleic acid coding for a polypeptide as defined in claim 1 comprising at least one base sequence selected from the group consisting of a first base sequence represented by SEQ ID NO: 8 and a second base sequence complementary to said first base sequence.

28. An isolated and purified deoxyribonucleic acid coding for a polypeptide as defined in claim 1 comprising at least one base sequence selected from the group consisting of a first base sequence represented by SEQ ID NO: 11 and a second base sequence complementary to said first base sequence.

* * * * *